(12) United States Patent
Broderick et al.

(10) Patent No.: US 7,395,607 B1
(45) Date of Patent: Jul. 8, 2008

(54) ROTATIONAL AND TRANSLATIONAL MICROPOSITION APPARATUS AND METHOD

(75) Inventors: Mark P. Broderick, Sarasota, FL (US); Sergei Petrenko, Kiev (UA); Alexander Raphalovitz, Sarasota, FL (US); Valentin Zhelyaskov, Sarasots, FL (US)

(73) Assignee: Discovery Technology International, LLLP, Sarasota, FL (US)

( * ) Notice: Subject to any disclaimer, the term of this patent is extended or adjusted under 35 U.S.C. 154(b) by 169 days.

(21) Appl. No.: 11/424,133

(22) Filed: Jun. 14, 2006

Related U.S. Application Data

(60) Provisional application No. 60/690,358, filed on Jun. 14, 2005.

(51) Int. Cl.
*G01B 5/008* (2006.01)
*G01B 7/008* (2006.01)
(52) U.S. Cl. .......................................... 33/566; 33/503
(58) Field of Classification Search .................. 33/556
See application file for complete search history.

(56) References Cited

U.S. PATENT DOCUMENTS

| | | | | |
|---|---|---|---|---|
| 4,477,973 A | * | 10/1984 | Davies | 33/1 CC |
| 4,807,152 A | * | 2/1989 | Lane et al. | 33/1 M |
| 5,410,817 A | * | 5/1995 | Kish | 33/559 |
| 6,125,337 A | * | 9/2000 | Rosenberg et al. | 702/153 |
| 6,354,012 B1 | * | 3/2002 | Pettersson | 33/503 |
| 6,546,643 B2 | * | 4/2003 | Lotze et al. | 33/559 |
| 6,606,539 B2 | * | 8/2003 | Raab | 33/503 |
| 7,076,883 B2 | * | 7/2006 | Yamamoto et al. | 33/556 |
| 2002/0069544 A1 | * | 6/2002 | McMurtry | 33/503 |
| 2004/0148791 A1 | * | 8/2004 | Eaton | 33/503 |
| 2007/0163134 A1 | * | 7/2007 | Eaton | 33/502 |

* cited by examiner

*Primary Examiner*—Christopher W Fulton
(74) *Attorney, Agent, or Firm*—Ronald E. Smith; Smith & Hopen, P.A.

(57) ABSTRACT

A rotational and translational microposition apparatus includes a first rotary motor, a second rotary motor and a linear motor. The first rotary motor surmounts an upstanding bracket mounted to a support surface. A rigid link having a right angle bend formed in it interconnects the first and second rotary motors to one another. A first end of the rigid link is secured to an output shaft of the first rotary motor and a second end of the rigid link is secured to a mounting plate to which is secured the second rotary motor. A linear motor has an output shaft connected to the output shaft of the second rotary motor. Selective operation of the three motors enables a probe to be positioned in an infinite plurality of positions that collectively form a cone where the tip of the probe is coincident with the vertex of the cone.

16 Claims, 8 Drawing Sheets

ROTATIONAL AND TRANSLATIONAL MICROPOSITION APPARATUS AND METHOD

CROSS-REFERENCES TO RELATED APPLICATIONS

This application claims the benefit of U.S. Provisional Application No. 60/690,358, with the same title and filed by the same inventors on Jun. 14, 2005.

BACKGROUND OF THE INVENTION

1. Field of the Invention

This invention relates, generally, to micropositioning devices. More particularly, it relates to a micropositioning device that maintains the tip of a probe in juxtaposition with a workpiece over an infinite number of positions of the probe.

2. Description of the Prior Art

Micropositioning devices have many applications. They are typically used when a job is too precise or too repetitive for human hands to perform.

In biology and physiology research, for example, the traditional method of positioning devices such as microsensors or microinjection probes relies upon commercially available XYZ micropositioners, also known as micromanipulators. However, the angle of approach of the probe of such instruments is typically pre-set and cannot readily be changed. The angle of approach of a probe, in other words, is usually coincident with one of the three orthogonally-disposed-apart axes.

Simple rotational devices such as a simple ball and socket type of adapter may be secured to the known XYZ micromanipulators. Such a device is usually secured to a single axis (typically the x-axis controlling the linear approach to the specimen). The position of such devices is pre-set by hand.

In the field of semiconductors, during reworking and prototyping of microchips it is necessary to approach areas of the chip using miniature test-tools. It is difficult to correct the angle of approach after the target site has been designated.

In the field of fiber optics it is often necessary to align the respective longitudinal axes of two optical fibers with one another to enable efficient transfer of light. Commercially available prior art devices enable XYZ positioning of fibers but do not enable angular alignment.

An XYZ positioning device is a typical micropositioning device. As its name implies, it can move a probe along an X-axis, a Y-axis, and a Z-axis so that the tip of the probe can be brought into juxtaposition with a location where a job is to be performed. However, whenever the probe's angle of approach is changed, manual repositioning of the tip of the probe is required.

It would be advantageous if a micropositioning device could position a tip of a probe at the location where work is to be performed for any angle of approach of the probe. Productivity would be substantially improved if a probe could approach a preselected location from an infinite number of angles of approach in the absence of manual repositioning.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for a means for an improved micropositioning device is now met by a new, useful, and non-obvious invention.

The novel rotational and translational micropositioning apparatus of this invention includes a first rotary motor having an output shaft that rotates about an axis of rotation in a horizontal plane.

An upstanding bracket is secured to a support surface and the first rotary motor is disposed in surmounting relation to the upstanding bracket. Accordingly, the position of the output shaft of the first rotary motor is a fixed position that never changes for any position of the probe that is under the control of the micropositioning device.

A second rotary motor has an output shaft that rotates about an axis of rotation that is in a horizontal plane only when the second rotary motor is in a position of repose.

A rigid link interconnects the first and second rotary motors to one another. The rigid link has a first end secured to the output shaft of the first rotary motor for conjoint rotation therewith. The rigid link has a second end and a right angle bend formed therein between the first and second ends.

A mounting plate is secured to the second end of the rigid link and the second rotary motor is mounted to the mounting plate. The axis of rotation of the output shaft of the first rotary motor is therefore orthogonally disposed to the axis of rotation of the output shaft of the second rotary motor. The respective axes of rotation of said first and second rotary motors lie in a common horizontal plane when the novel apparatus is in its position of repose.

A linear motor having a straight output shaft is secured to the output shaft of the second rotary motor for conjoint rotation therewith. The linear motor travels in a first linear direction away from the second rotary motor when the linear motor is operating in a first direction and in a second linear direction opposite to the first linear direction when the linear motor is operating in the second direction. The linear motor travels along a straight path of travel in a first and a second direction.

When the second rotary motor is in its position of repose, the linear motor rotates in a vertical plane in a first direction when the output shaft of the second rotary motor rotates in said first direction and said linear motor rotates in said vertical plane in an opposite direction to said first direction when said output shaft of the second rotary motor rotates in said second direction.

A probe of linear configuration having a tip at its leading end is clamped to the linear motor in parallel relation to the linear motor so that a longitudinal axis of symmetry of the probe is parallel to a translational axis of the linear motor;

The apparatus has a position of repose where the output shaft of the first rotary motor and the output shaft of the second rotary motor are disposed in a horizontal plane in orthogonal relation to one another and the output shaft of the linear motor is disposed in a vertical plane in orthogonal relation to the output shaft of the second rotary motor. The probe is displaced in a first linear direction when the linear motor operates in the first linear direction and the probe is displaced in a second linear direction when the linear motor operates in the second linear direction.

A virtual point is defined where the axis of rotation of the first and second rotary motors and the longitudinal axis of symmetry of the probe intersect when the apparatus is in the position or repose. Significantly, the tip of the probe remains in juxtaposition with the virtual point for any angle of approach of the probe to said virtual point, in the absence of manual repositioning.

In a preferred embodiment, the first rotary motor, the second rotary motor, and the linear motor are piezoelectric motors and each motor therefore has a piezo element. A control unit supplies resonant frequency excitation pulses of controlled duration to the respective piezo element of each of the motors. A joystick may be electrically coupled to the control unit to enable manual control of the first, second, and third motors. Alternatively, a programmed computer may control the operation of the motors.

Rotation of the output shaft of the first rotary motor in a first direction effects conjoint rotation of the second rotary motor in a vertical plane when the second rotary motor and the linear motor are not operating. Rotation of the output shaft of the first rotary motor in a second direction effects conjoint rotation of the second rotary motor in said vertical plane when the second rotary motor and said linear motor are not operating.

Rotation of the output shaft of the second rotary motor in a first direction when said first rotary motor is not operating effects conjoint rotation of the linear motor in the first direction in a vertical plane and rotation of the output shaft of the second rotary motor in a second direction opposite to the first direction when the first rotary motor is not operating effects conjoint rotation of the linear motor in the second direction in a vertical plane;

Simultaneous selective rotation of the respective output shafts of the first and second rotary motors and simultaneous displacement of the linear motor relative to its output shaft enables the probe to be positioned in an infinite plurality of infinite positions of adjustment.

The infinite plurality of positions of adjustment collectively defines a cone where the tip of the probe defines the vertex of the cone. An angle $\alpha$ is defined as the angle between the longitudinal axis of symmetry of the probe when in a vertical position of repose and the longitudinal axis of symmetry of the probe when said probe is not in its position of repose. The probe may approach the workpiece from an infinite number of positions of approach and the collective form of said infinite number of approaches may be pictured as a cone where the axis of the cone in coincident with the longitudinal axis of symmetry of the probe when said probe is in said position of repose.

The primary advantage of the novel micropositioning device is that the probe may approach the workpiece from any angle of approach and no manual repositioning of the tip of the cone is required when the angle of approach is changed.

This and other advantages will become apparent as this disclosure proceeds. The invention includes the features of construction, arrangement of parts, and combination of elements set forth herein, and the scope of the invention is set forth in the claims appended hereto.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
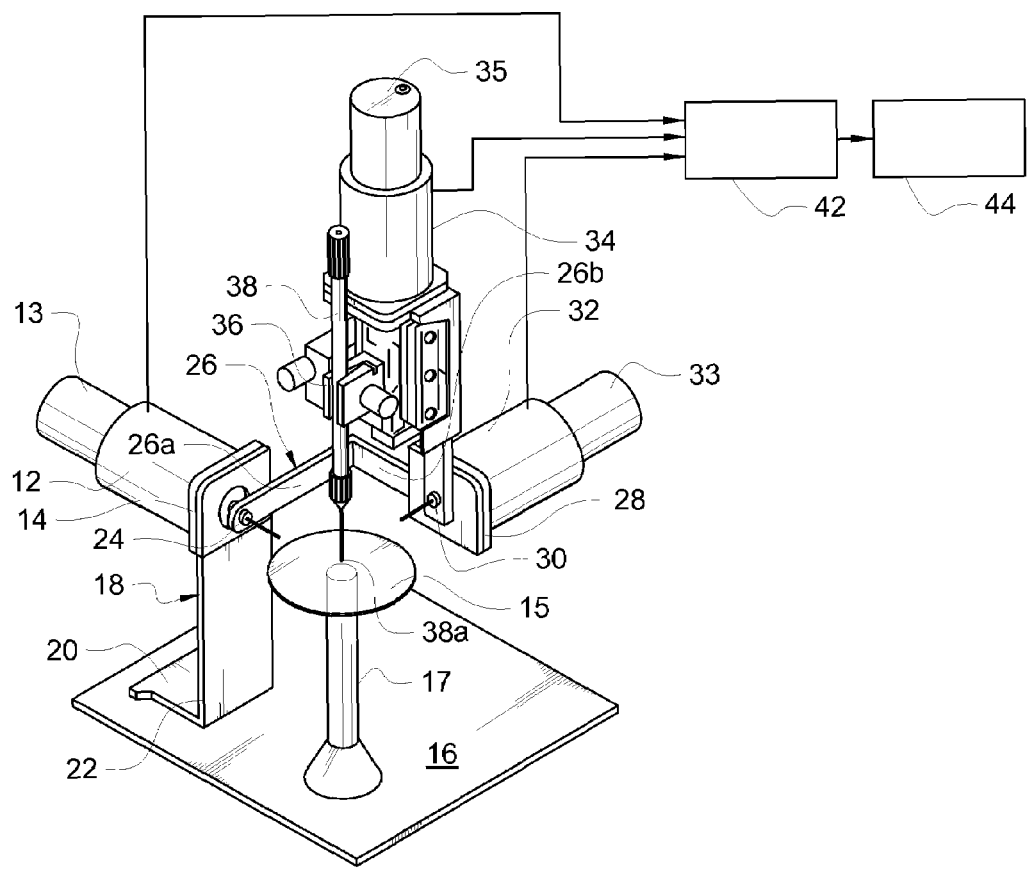
FIG. 1 is a perspective view of the novel micropositioning device when in a position of repose.

Referring now to FIG. 1, it will there be seen that an illustrative embodiment of the invention is denoted as a whole by the reference numeral 10.

Apparatus 10, to be sold commercially under the trademark Robomate, is a hybrid (rotational-translational) micro-positioning device. The novel apparatus provides an enhanced level of positioning by combining a range of movements in spherical and linear coordinates. It is depicted in its position of repose in FIG. 1.

It should be understood that the structure and method disclosed herein is applicable to micropositioning and nanopositioning devices. All references to micropositioning are therefore understood to include nanopositioning as well, both in this specification and in the claims appended hereto.

Apparatus 10 includes two (2) rotary and one (1) translation (linear) motors, preferably piezoelectric motors. First rotary motor 12 includes output shaft 14 and is vertically elevated from support surface 16 by stationary upstanding bracket 18 having a flat truncate part 20 secured to said support surface 16 and a flat elongate part 22. Opening 24 is formed in flat elongate part 22 near its distal free end and said opening 24 accommodates output shaft 14.

Note that first rotary motor 12 cannot move because it is fixedly secured in surmounting relation to upstanding bracket 18. Accordingly, the axis of rotation of output shaft 14 remains in a fixed position throughout all movements of device 10.

Rigid arm 26 includes a first part 26a that is apertured near its proximal end to engage output shaft 14 of first rotary motor 12. Rigid arm 26 further includes second part 26b that is formed integrally with first part 26a and which is disposed orthogonally thereto. Second part 26b is formed integrally with flat mounting plate 28 which is centrally apertured to receive therethrough output shaft 30 of second rotary motor 32. Said second rotary motor 32 is mounted to flat mounting plate 28 in cantilevered relation thereto.

Accordingly, the axis of rotation of output shaft 14 is orthogonal to the axis of rotation of output shaft 30 when apparatus 10 is in said position of repose. An imaginary extension of both of said axes of rotation, depicted in dotted lines, meets at an unnumbered point referred to as the virtual point.

Platform 15 is supported by pedestal 17. A workpiece to be worked upon by probe 38 is secured to table 15 so that said workpiece is coincident with the virtual point.

Platform 15 may be rotated in a horizontal plane about its vertical axis and displaced vertically along its longitudinal axis. Moreover, its instantaneous position may be under the control of an X, Y, Z positioning device, thereby enabling an unlimited number of positions of the workpiece with respect to tip 38a of probe 38.

Third motor 34 is a linear displacement micropositioner. It has a straight output shaft that is apertured at its proximal end to engage output shaft 30 of second rotary motor 32. The axis of displacement of third motor 34 is at a right angle to the axis of rotation of output shaft 30. Clamp 36 secures probe 38 in spaced apart, parallel relation to linear motor 32. The longitudinal axis of symmetry of probe 38 is parallel to the translational axis of linear motor 34.

The spacing between probe 38 and linear motor 34 is preselected so that when apparatus 10 is in its position of repose as depicted in FIG. 1, the longitudinal axis of symmetry of probe 38 intersects the respective longitudinal axes of symmetry of output shafts 14 and 30 of the first and second rotary motors.

The point of intersection of said three (3) axes is hereinafter referred to as the virtual point.

When probe 38 is in its position of repose, tip 38a of said probe 38 is in juxtaposition with the virtual point. Significantly, when probe 38 is not in said position of repose, i.e., when it is disposed at an angle relative to its FIG. 1 position, tip 38a of said probe remains in juxtaposition with said virtual point. This holds true for every angle of approach to said virtual point and there is never a need to manually reposition the tip of the probe when the angle of approach of the probe changes. The virtual point is not numbered to avoid confusing it with probe tip 38a.

Any suitable tool or electrode may replace probe 38 or a suitable tool or electrode may be mounted to said probe in coincidence with the longitudinal axis of symmetry of said probe. Accordingly, probe 38 may be referred to as probe/tool/electrode 38 but hereinafter is called probe/tool 38.

The depicted FIG. 1 position is the position of repose because rigid arm 26 is disposed in a horizontal plane, second rotary motor 32 is in a horizontal plane, linear motor 34 and probe/tool 38 are disposed in a vertical plane, and the longitudinal axis of probe/tool 38 and the respective axes of rotation of the output shafts of the first and second rotary motors intersects virtual point as aforesaid.

Figure 2:
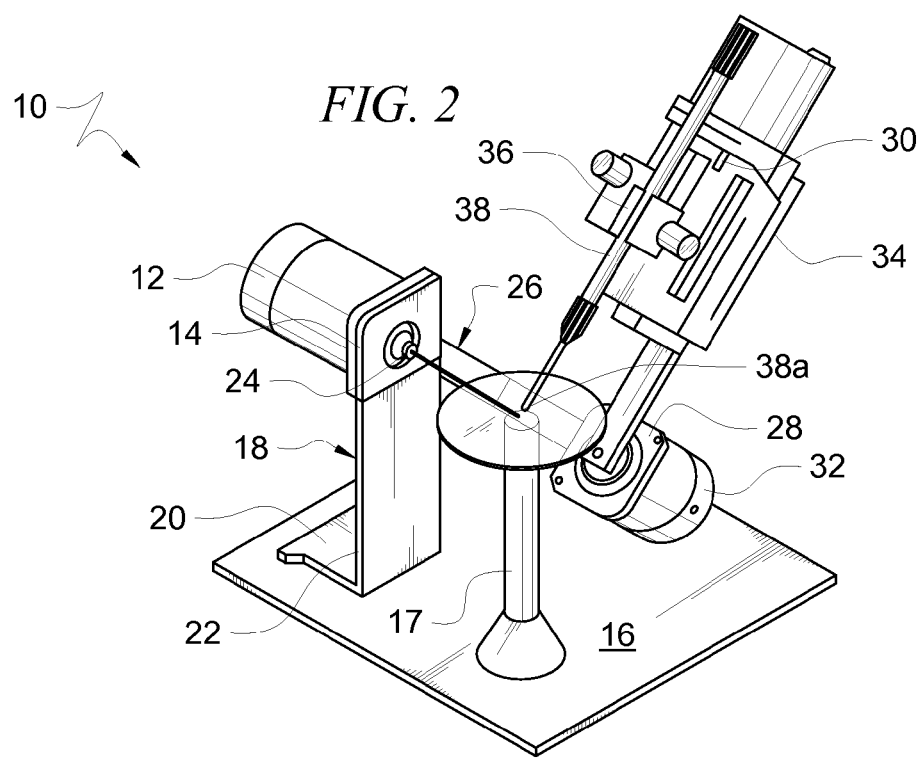
FIG. 2 is a perspective view depicting the novel apparatus when the output shaft of a first rotary motor is rotated in a first direction while the output shaft of the second rotary motor is not rotated.

FIG. 2 depicts a non-repose position where output shaft 14 of first rotary motor 12 has rotated in a first direction (clockwise as viewed from the virtual point). The output shafts of second rotary motor 32 and linear motor 34 remain in their respective unrotated positions of repose. Significantly, in the set-up of FIGS. 1-6, tip 38a remains in juxtaposition with the virtual point at all times when said first rotary motor 12 is operating.

Figure 3:
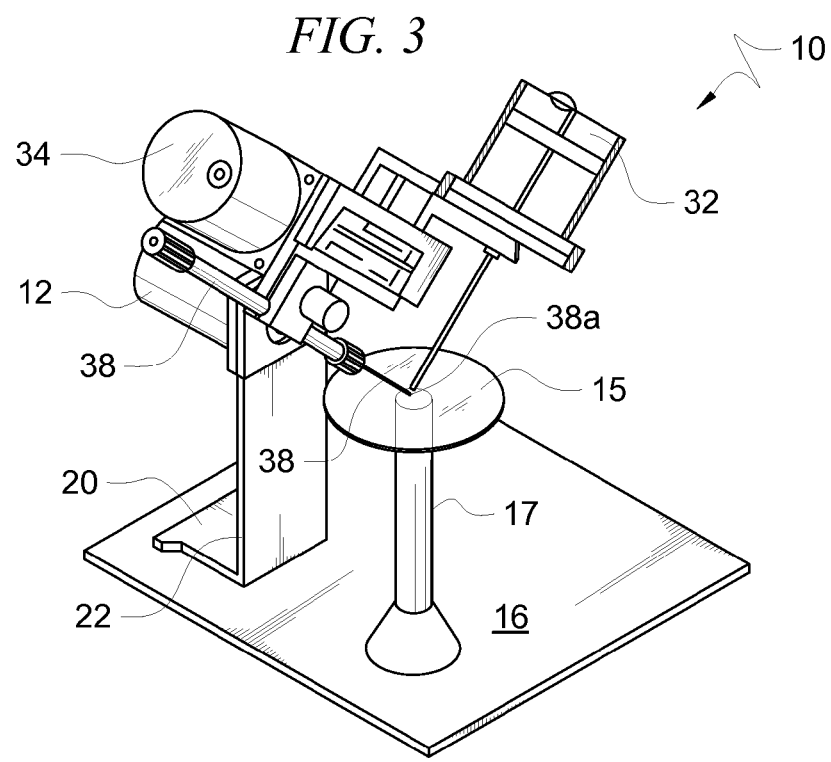
FIG. 3 is a perspective view depicting the novel apparatus when the output shaft of the first rotary motor is rotated in a second direction opposite to said first direction while the output shaft of the second rotary motor is not rotated.

FIG. 3 depicts a non-repose position where output shaft 14 of first rotary motor 12 has rotated in a second direction (counterclockwise as viewed from the virtual point). The output shafts of second rotary motor 32 and linear motor 34 remain in their respective unrotated positions of repose.

Figure 4:
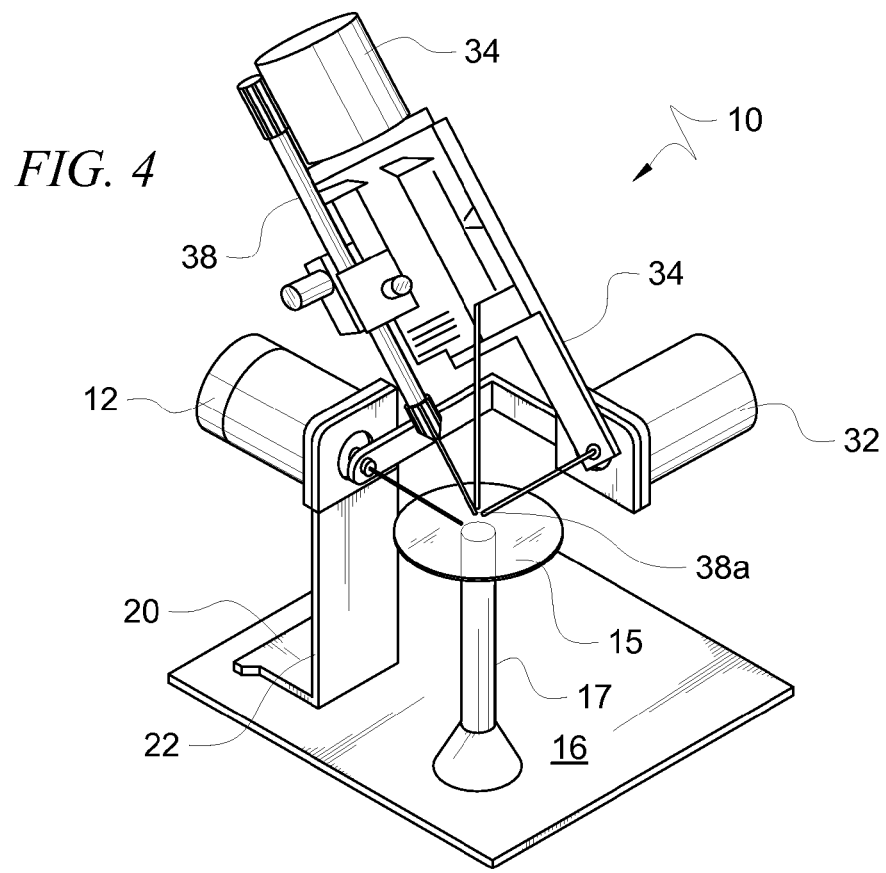
FIG. 4 is a perspective view depicting the novel apparatus when the output shaft of the second rotary motor is rotated in a first direction while the output shaft of the first rotary motor is not rotated.

FIG. 4 depicts a non-repose position where output shaft 30 of second rotary motor 32 has rotated in a first direction (counterclockwise as viewed from the virtual point). The output shafts of first rotary motor 12 and linear motor 34 remain in their respective unrotated positions of repose.

Figure 5:
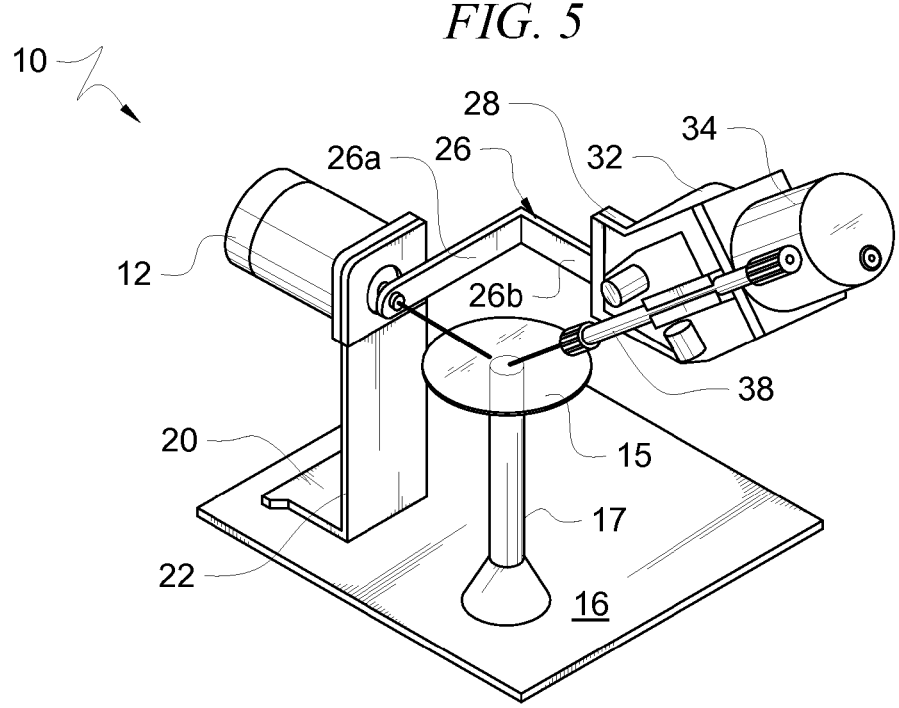
FIG. 5 is a perspective view depicting the novel apparatus when the output shaft of the second rotary motor is rotated in a second direction opposite to said first direction while the output shaft of the first rotary motor is not rotated.

FIG. 5 depicts a non-repose position where output shaft 30 of second rotary motor 32 has rotated in a second direction (clockwise as viewed from the virtual point). The output shafts of first rotary motor 12 and linear motor 34 remain in their respective unrotated positions of repose.

Figure 6:
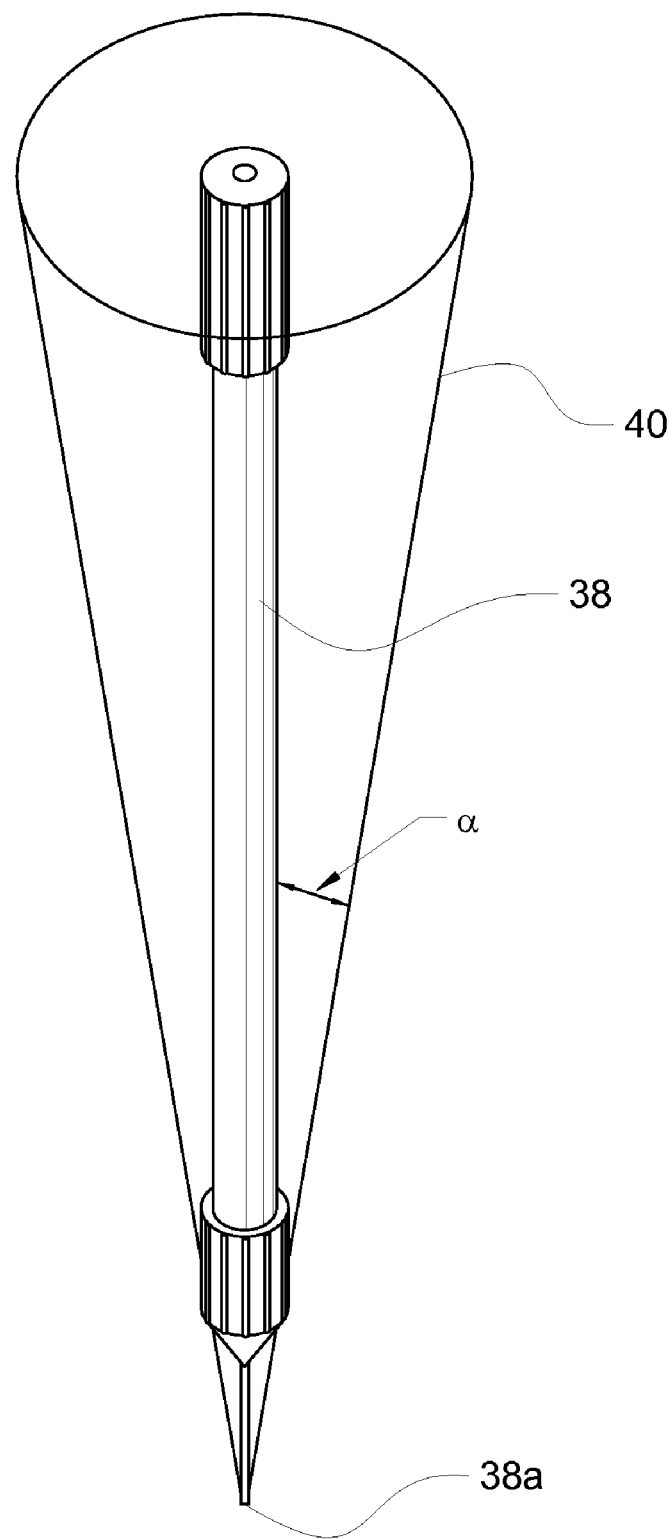
FIG. 6 is a perspective view depicting the novel probe in its position of repose at the center of a cone where the cone represents an infinite number of positions of adjustment into which the probe may be positioned by cooperative operation of said first and second rotary motors and said linear motor.

FIG. 6 is a perspective view depicting novel probe/tool 38 at the longitudinal axis of symmetry of a cone 40 where cone 40 represents an infinite number of positions of adjustment into which probe/tool 38 may be positioned by cooperative operation of said first and second rotary motors and said linear motor. Significantly, tip 38a remains in juxtaposition with the virtual point at all times when said three (3) motors are operating. Novel apparatus 10 enables angular micro-movement within conical space 40. Tip 38a of probe/tool 38 must remain in registration with the virtual point during probe movement for cone 40 to be generated. Angle α indicates the angular range of motion of probe/tool 38.

Figure 7A:
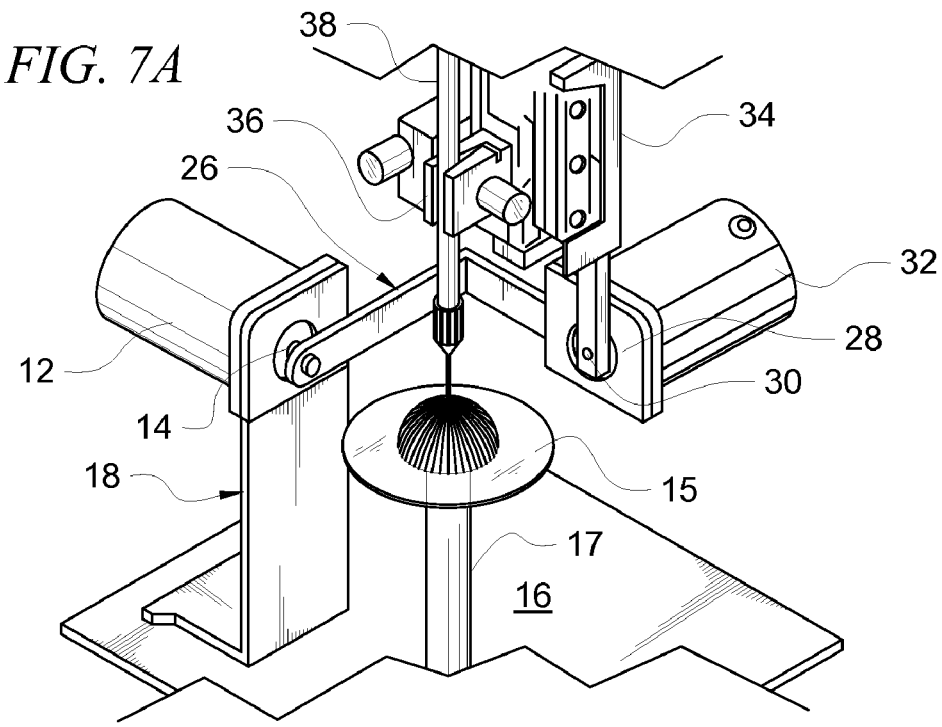
FIG. 7A is a perspective view depicting a downwardly opening, convex hemisphere that represents an infinite number of positions of adjustment into which the tip of the probe may be positioned by cooperative operation of said first and second rotary motors and said linear motor when said tip is elevated above the virtual point.

FIG. 7A is a perspective view depicting a convex or downwardly-opening hemisphere that represents an infinite number of positions of adjustment into which tip 38a of probe/tool 38 may be positioned by cooperative operation of said first and second rotary motors and said linear motor when said tip 38a is elevated above the virtual point. Significantly, tip 38a remains in its elevated position relative to the virtual point at all times when said three (3) motors are operating.

Figure 7B:
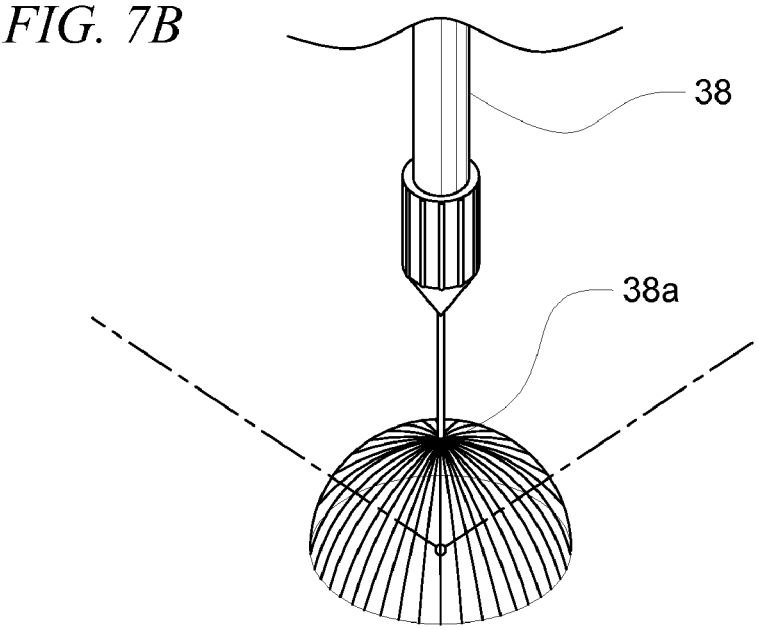
FIG. 7B is a perspective view of the downwardly-opening convex hemisphere of FIG. 7A when viewed from a perspective below the virtual point and depicting the probe displaced away from its position of repose.
Figure 7C:
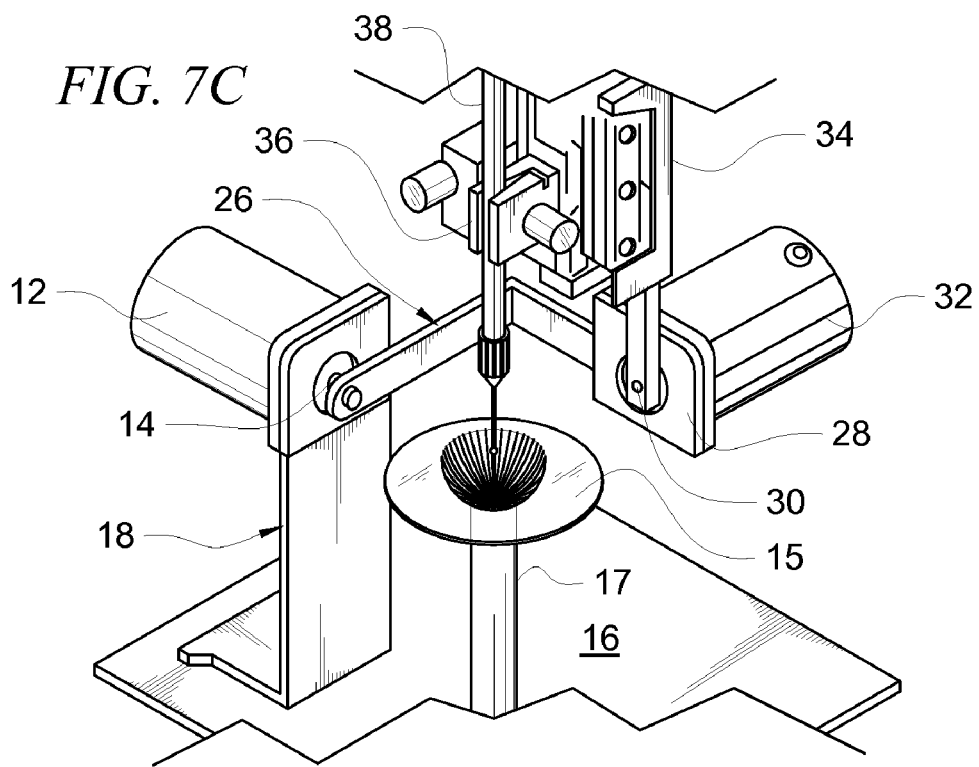
FIG. 7C is a perspective view depicting an upwardly opening, concave hemisphere that represents an infinite number of positions of adjustment into which the tip of the probe may be positioned by cooperative operation of said first and second rotary motors and said linear motor when said tip is positioned below the virtual point.

FIG. 7B is a perspective view of the downwardly-opening convex hemisphere of FIG. 7A when viewed from a perspective below the virtual point and depicting the probe displaced away from its position of repose;

FIG. 7C is a perspective view depicting a concave or upwardly-opening hemisphere that represents an infinite number of positions of adjustment into which tip 38a of probe/tool 38 may be positioned by cooperative operation of said first and second rotary motors and said linear motor when said tip 38a is positioned below the virtual point.

Figure 7D:
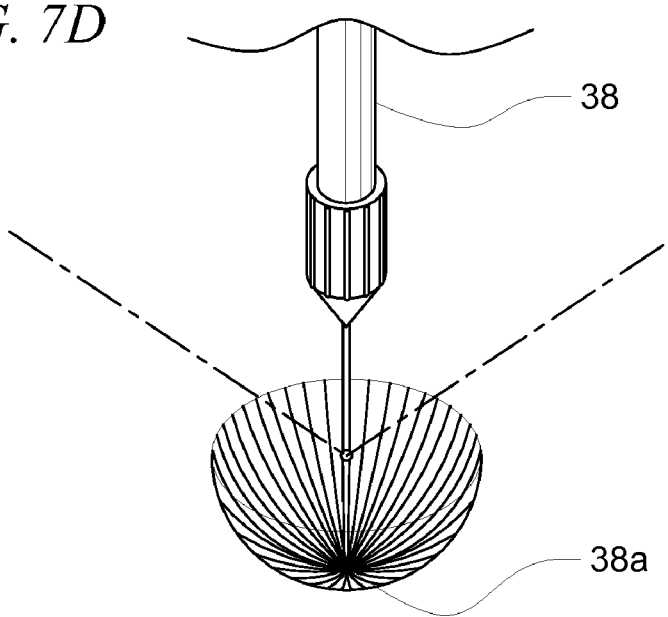
FIG. 7D is a perspective view of the upwardly-opening concave hemisphere of FIG. 7C when viewed from a perspective above the virtual point and depicting the probe in its position of repose.

FIG. 7D is a perspective view of the upwardly-opening concave hemisphere of FIG. 7C when viewed from a perspective above the virtual point and depicting the probe in its position of repose below said virtual point.

Returning now to FIG. 1, it will there be seen that control unit 42 supplies resonant frequency excitation pulses of controlled duration to the piezo element of each of the three (3) piezoelectric motors. Joystick 44 is fitted to control unit 42 and is used to facilitate the manual control of all three (3) motors.

A programmed computer may also be employed to control the novel apparatus. Whether computer or joystick controlled, the angles of rotation of each output shaft of each rotary motor and the amount of linear translation of the linear motor is specifically controlled.

FIG. 1 also depicts an improved embodiment of hybrid micropositioning apparatus 10. In the improved embodiment, an optical encoder is mounted externally on each of the three (3) motors. Said optical encoders are respectively denoted 13, 33, and 35 in said FIG. 1. Alternatively, the optical encoders are mounted internally and integrated with each of the three (3) motors. FIG. 1 is the only drawing depicting the encoders in their externally mounted configuration.

An improved embodiment further includes a controller based on digital signal processing (DSP) technology. The optical encoders and DSP controller are connected to a programmed computer to enable control of the absolute rotational or linear coordinates of the motors. The computer therefore controls the instantaneous rotational positions of the respective output shafts of the two rotary motors as well as the instantaneous linear position of output shaft of linear motor 34 and hence of probe/tool 38. This mechanism for moving the output shafts of the rotary and linear motors at specific angles and linear positions, respectively, is reproducible and within the accuracy of the respective motors.

Novel apparatus 10 can be attached to an XYZ positioning device to enhance the performance of said novel apparatus. The XYZ positioning device enables tip 38*a* of probe 38 (or the tip of any electrode or tool that is substituted for said probe) to be positioned at the point of application (the virtual point) in three-dimensional (3-D) space, as determined by the specifications of the XYZ positioning device. When the point of application is reached, the angle of approach of novel probe/tool 38 is changed by rotational operation of either rotary motor while maintaining the position of tip 38*a* continuously at the point of application. This capability constitutes a substantial improvement over existing rotational systems attached to XYZ micropositioners because such known systems require manual repositioning of the tip 38*a* of the probe/tool 38 for every change in the angle of approach as mentioned earlier. Substantial productivity gains are realized when such manual repositioning is eliminated.

Although piezoelectric motors are preferred, any rotary motor (e.g., a DC servo motor, a stepper motor, and the like) is within the scope of this invention.

Maximum performance requires that the rotary motor selected must have a substantial self-deceleration torque. Higher self-deceleration torque allows implementing the positioning (rotation) with higher speed and adequate minimum stopping time, and at the same time provides a braking mechanism for positioning each rotary motor in a particular angular orientation between movements. The preferred piezoelectric motor is disclosed in co-pending U.S. patent application US 2005/0023930.

The enhanced positioning capabilities of the novel apparatus have important applications in the fields of biology, physiology, medicine, photonics, fiber optics, microelectronics and the semi-conductor industry.

The novel method for rotationally and translationally micropositioning a linear probe includes the steps of providing a support surface, securing an upstanding bracket to the support surface, mounting a first rotary motor having an output shaft that rotates about an axis of rotation in a horizontal plane in surmounting relation to the upstanding bracket, providing a second rotary motor having an output shaft that rotates about an axis of rotation, interconnecting the first and second rotary motors to one another with a rigid link having a first end, a second end, and a right angle bend formed therein between the first end and the second end, securing the first end of the rigid link to the output shaft of the first rotary motor for conjoint rotation therewith and securing a mounting plate to the second end of the rigid link. The method further includes the steps of mounting the second rotary motor to the mounting plate and disposing the axis of rotation of the output shaft of the second rotary motor in orthogonal relation to the axis of rotation of the output shaft of the first rotary motor.

The novel method further includes the steps of providing a linear motor having a straight output shaft and mounting the straight output shaft to the output shaft of the second rotary motor for conjoint rotation therewith so that the linear motor travels in a first linear direction when the linear motor is operating in a first direction and so that the linear motor travels in a second linear direction opposite to the first linear direction when the linear motor is operating in the second direction.

The novel method further includes the steps of providing a probe of linear configuration having a tip, clamping the probe to the linear motor in parallel relation to the linear motor so that a longitudinal axis of symmetry of the probe is parallel to a translational axis of the linear motor, operating the linear motor in a first linear direction to displace the probe in the first linear direction and operating the linear motor in a second linear direction opposite to the first linear direction to displace the probe in the second linear direction, rotating the output shaft of the first rotary motor in a first direction to effect conjoint rotation of the second rotary motor in a vertical plane when the second rotary motor and the linear motor are not operating, rotating the output shaft of the first rotary motor in a second direction to effect conjoint rotation of the second rotary motor in the vertical plane when the second rotary motor and the linear motor are not operating, rotating the output shaft of the second rotary motor in a first direction when the first rotary motor is not operating to effect conjoint rotation of the linear motor in the first direction in a vertical plane, and rotating the output shaft of the second rotary motor in a second direction opposite to the first direction when the first rotary motor is not operating to effect conjoint rotation of the linear motor in the second direction in a vertical plane so that simultaneous rotation of the output shaft of the first rotary motor, the output shaft of the second rotary motor, and simultaneous displacement of the linear motor relative to its output shaft enable the probe to be positioned in an infinite plurality of positions of adjustment where the tip of the probe remains in juxtaposition with a virtual point and so that the infinite plurality of positions of adjustment collectively define a cone where the tip of the probe defines the vertex of the cone.

The novel method further includes the steps of positioning the tip of the probe so that it forms at least a first, downwardly opening, convex hemispherical path of travel relative to the virtual point by elevating the tip of the probe relative to the virtual point and by cooperative operation of the first and second rotary motors and said linear motor. The method further includes the steps of positioning the tip of the probe so that it forms a plurality of downwardly opening, convex hemispherical paths of travel relative to the virtual point, in addition to said at least a first, downwardly opening, convex hemispherical path of travel by elevating the tip of the probe relative to the virtual point and by cooperative operation of the first and second rotary motors and the linear motor.

The novel method further includes the steps of positioning the tip of the probe so that it forms at least a second, upwardly opening, concave hemispherical path of travel relative to the virtual point by positioning the tip of the probe below the virtual point and by cooperative operation of the first and second rotary motors and said linear motor. The method further includes the steps of positioning the tip of the probe so that it forms a plurality of upwardly opening, concave hemispherical paths of travel relative to the virtual point, in addition to said at least a first, upwardly opening, concave hemispherical path of travel by positioning the tip of the probe below the virtual point and by cooperative operation of the first and second rotary motors and the linear motor.

The method steps further includes the steps of providing each of the motors in the form of a piezoelectric motor, each of which is provided with a piezo element, and supplying resonant frequency excitation pulses of controlled duration to the respective piezo element of each of the motors.

Further method steps include the steps of electrically coupling a joystick to the control unit to enable manual control of the first, second, and third motors or, in the alternative, controlling the apparatus with a programmed computer.

Still further method steps include the steps of attaching the novel apparatus to a conventional XYZ positioning device to enhance the performance of said novel apparatus.

The apparatus depicted in FIG. 1 overcomes the drawbacks of prior art devices by enabling a continuously variable angle of approach while keeping end point 38a of probe 38 in the same XYZ coordinate (virtual point) during rotation. This is possible only if the longitudinal axis of symmetry of probe/tool 38 and end point 38a are aligned with the intersect (the virtual point) of the axes of rotation of output shafts 14 and 30 of first and second rotary motors 12 and 32, respectively.

Figure 8A:
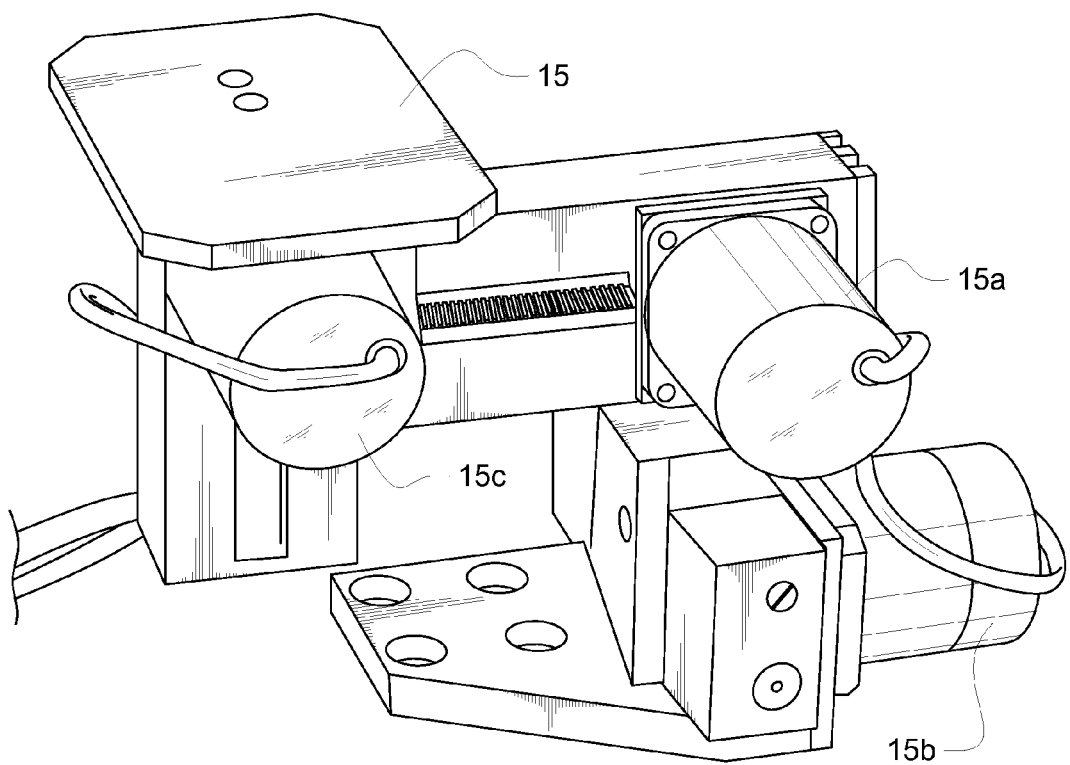
FIG. 8A is a perspective view of three motors that respectively control the instantaneous position of the platform in the x, y, and z axes.
Figure 8B:
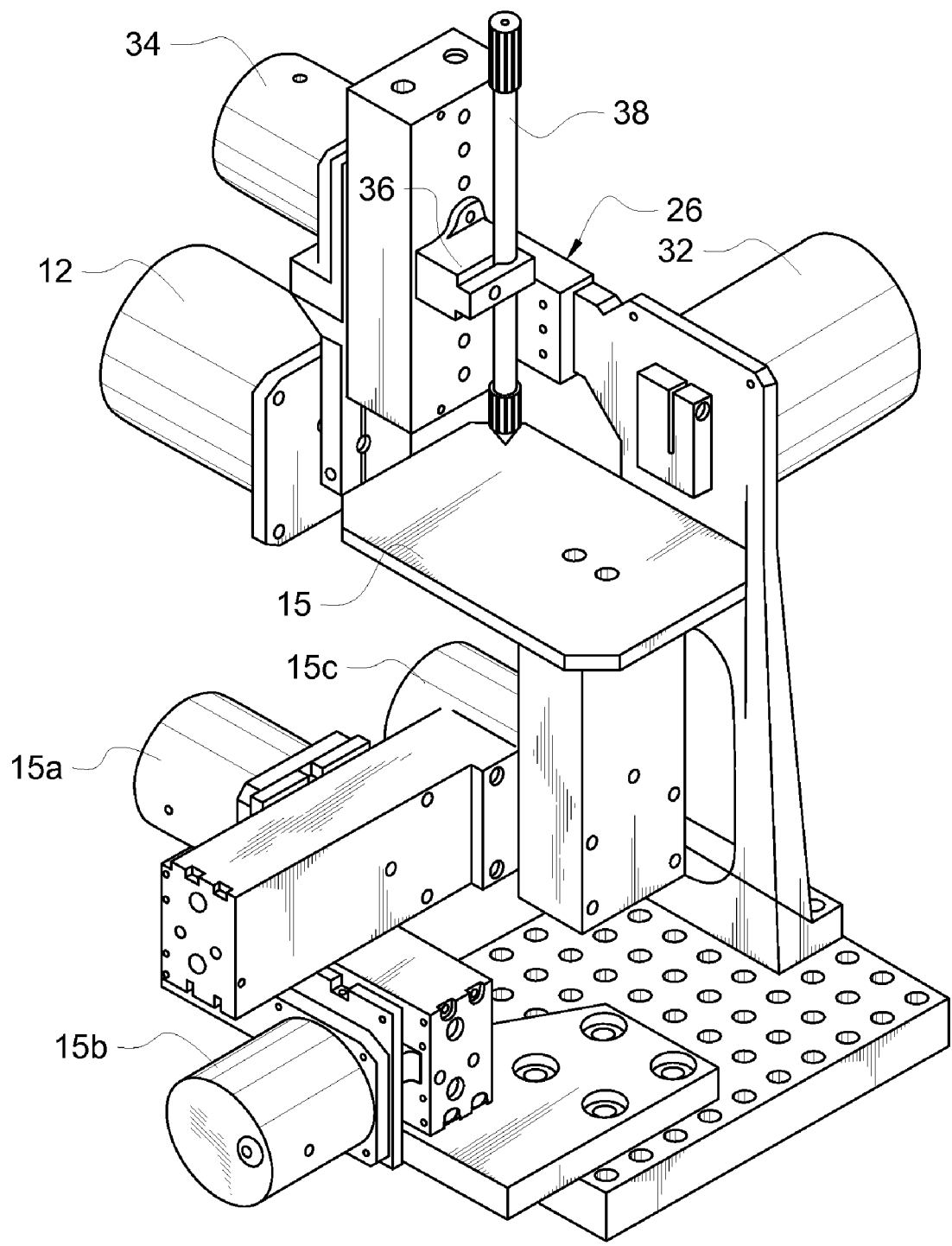
FIG. 8B depicts the three motors of FIG. 8A in the context of the three motors that control the instantaneous position of the platform.

In a further embodiment, the position of platform 15 is under the control of motors 15a, 15b, and 15c as depicted in FIG. 8A so that said platform may be moved with precision in the x, y, and z axes, respectively, by said motors. This increases the versatility of the apparatus. FIG. 8B depicts the parts disclosed in FIG. 8A together with the parts disclosed in FIGS. 1-5.

Motors 15a, 15b, and 15c enable platform 15, in conjunction with apparatus 10, to position an animal within stereotaxic calculated coordinates. When platform 15 is used as a stereotaxic positioner, it may be used during animal surgery applications and possibly clinical use as well. The motors enable computer control over the precise x, y, z movement.

Platform 15 may be adapted so that it is equipped with a stereotaxis frame (for example, for rodents such a frame would include ear bars and a mouth support that are used to keep the head perfectly still during a surgical procedure). Computer control of the system enables the preparation under study to be automatically and precisely located with respect to a surgical tool under the direct control of apparatus 10.

To perform an intra-cranial microinjection, the surgeon fixes the microinjector onto apparatus 10, places the anaesthetized preparation onto platform 15 and employs the stereotaxic frame to hold it against movement. The surgeon then enters or programs the stereotaxic coordinates, provided in various anatomical atlases, pertaining to a specific region of the brain in which the microinjection is to be administered. Platform 15 then moves to the specified position. The microinjector is aligned with the desired injection site by a combination of computer control of apparatus 10 and platform 15. Apparatus 10 then administers the microinjection.

Advantageously, apparatus 10 provides control over both angular and linear positioning of the tool. Moreover, the use of computer control enables the entire set of coordinates for any given procedure to be saved and recalled later. This greatly improves over the current method of manual positioning and calculations.

Apparatus 10 also has utility in microscopy applications. A microscope is fitted on linear arm 38, and the field of focus is centered on the virtual point. Changes in the angular position of the microscope will not affect the focus of the microscope.

Apparatus 10 may also be used in clinical treatment, biomedical research, and other fields to direct a radiation source or laser. This invention of course includes applications not expressly mentioned herein as a matter of law.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A rotational and translational micropositioning apparatus, comprising:
    a first rotary motor having an output shaft that rotates about an axis of rotation in a horizontal plane;
    a second rotary motor having an output shaft that rotates about an axis of rotation in a horizontal plane when said second rotary motor is in a position of repose;
    a support surface;
    an upstanding bracket secured to said support surface;
    said first rotary motor being disposed in surmounting relation to said upstanding bracket;
    a rigid link that interconnects said first and second rotary motors to one another;
    said rigid link having a first end secured to said output shaft of said first rotary motor for conjoint rotation therewith;
    said rigid link having a second end;
    said rigid link having a right angle bend formed therein between said first end and said second end;
    a mounting plate secured to said second end of said rigid link;
    said second rotary motor mounted to said mounting plate;
    said axis of rotation of the output shaft of said first rotary motor being orthogonally disposed to the axis of rotation of the output shaft of the second rotary motor;
    said apparatus having a position of repose where said output shaft of said first rotary motor and said output shaft of said second rotary motor are disposed in a common horizontal plane at a right angle to one another;
    a virtual point being defined where said respective axes of rotation intersect when said apparatus is in said position of repose; and
    said respective axes of rotation intersecting one another external to said first and second rotary motors.

2. The apparatus of claim 1, further comprising:
    a linear motor having a straight output shaft so that said that said linear motor travels along a straight path of travel;
    said straight output shaft being secured to said output shaft of said second rotary motor for conjoint rotation therewith so that said linear motor travels in a first linear direction when said linear motor is operating in a first direction and so that said linear motor travels in a second linear direction opposite to said first linear direction when said linear motor is operating in said second direction;
    a probe of linear configuration having a tip;
    a clamp for securing said probe to said linear motor in parallel relation to said linear motor so that a longitudinal axis of symmetry of said probe is parallel to a translational axis of said linear motor;
    said apparatus having a position of repose where said output shaft of said first rotary motor and said output shaft of said second rotary motor are disposed in a horizontal plane in orthogonal relation to one another and said output shaft of said linear motor is disposed in a vertical plane in orthogonal relation to said respective output shafts of said first and second rotary motors;

said probe being displaced in a first linear direction when said linear motor operates in said first linear direction and said probe being displaced in a second linear direction when said linear motor operates in said second linear direction;

whereby rotation of said output shaft of said first rotary motor in a first direction effects conjoint rotation of said second rotary motor in a vertical plane when said second rotary motor and said linear motor are not operating;

whereby rotation of said output shaft of said first rotary motor in a second direction effects conjoint rotation of said second rotary motor in said vertical plane when said second rotary motor and said linear motor are not operating;

whereby rotation of said output shaft of said second rotary motor in a first direction when said first rotary motor is not operating effects conjoint rotation of said linear motor in said first direction in a vertical plane;

whereby rotation of said output shaft of said second rotary motor in a second direction opposite to said first direction when said first rotary motor is not operating effects conjoint rotation of said linear motor in said second direction in a vertical plane;

whereby simultaneous rotation of said output shaft of said first rotary motor, said output shaft of said second rotary motor, and simultaneous displacement of said linear motor enable said probe to be positioned in an infinite plurality of angular and linear positions of adjustment; and whereby said infinite plurality of positions of adjustment collectively define a cone where said tip of said probe defines the vertex of said cone when said tip of said probe remains in juxtaposition with said virtual point.

3. The apparatus of claim 2, further comprising:
said first rotary motor, said second rotary motor, and said linear motor being piezoelectric motors; and
each of said piezoelectric motors having a piezo element.

4. The apparatus of claim 3, further comprising:
a control unit for supplying resonant frequency excitation pulses of controlled duration to the respective piezo element of each of said motors.

5. The apparatus of claim 4, further comprising:
a joystick electrically coupled to said control unit to enable manual control of said first, second, and third motors.

6. A method for rotationally and translationally micropositioning a linear probe, comprising the steps of:
providing a support surface;
securing an upstanding bracket to said support surface;
mounting a first rotary motor having an output shaft that rotates about an axis of rotation in a horizontal plane in surmounting relation to said upstanding bracket;
providing a second rotary motor having an output shaft that rotates about an axis of rotation in a horizontal plane when said second rotary motor is in a position of repose;
interconnecting said first and second rotary motors to one another with a rigid link having a first end secured to said output shaft of said first rotary motor for conjoint rotation therewith, having a second end, and having a right angle bend formed therein between said first end and said second end;
securing a mounting plate to said second end of said rigid link;
mounting said second rotary motor to said mounting plate; and
disposing said axis of rotation of the output shaft of said first rotary motor in orthogonal relation to the axis of rotation of the output shaft of the second rotary motor so that the axis of rotation of the output shaft of said first rotary motor and the axis of the rotation of the output shaft of said second rotary motor intersection one another at a virtual point that is external to said first and second rotary motors.

7. The method of claim 6, further comprising:
providing a linear motor having a straight output shaft;
mounting said straight output shaft to said output shaft of said second rotary motor for conjoint rotation therewith so that said linear motor travels in a first linear direction when said linear motor is operating in a first direction and so that said linear motor travels in a second linear direction opposite to said first linear direction when said linear motor is operating in said second direction;
providing a probe of linear configuration having a tip;
clamping said probe to said linear motor in parallel relation to said linear motor so that a longitudinal axis of symmetry of said probe is parallel to a translational axis of said linear motor;
operating said linear motor in a first linear direction to displace said probe in said first linear direction and operating said linear motor in a second linear direction opposite to said first linear direction to displace said probe in said second linear direction;
rotating said output shaft of said first rotary motor in a first direction to effect conjoint rotation of said second rotary motor in a vertical plane when said second rotary motor and said linear motor are not operating;
rotating said output shaft of said first rotary motor in a second direction to effect conjoint rotation of said second rotary motor in said vertical plane when said second rotary motor and said linear motor are not operating;
rotating said output shaft of said second rotary motor in a first direction when said first rotary motor is not operating to effect conjoint rotation of said linear motor in said first direction in a vertical plane;
rotating said output shaft of said second rotary motor in a second direction opposite to said first direction when said first rotary motor is not operating to effect conjoint rotation of said linear motor in said second direction in a vertical plane;
whereby simultaneous rotation of said output shaft of said first rotary motor, said output shaft of said second rotary motor, and simultaneous displacement of said linear motor enable said probe to be positioned in an infinite plurality of infinite positions of adjustment where said tip of said probe remains in juxtaposition with said virtual point; and
whereby said infinite plurality of positions of adjustment collectively define a cone where said tip of said probe defines the vertex of said cone.

8. The method of claim 7, further comprising the steps of:
positioning said tip of said probe so that it forms at least a first hemispherical path of travel relative to said virtual point by elevating said tip of said probe relative to said virtual point and by cooperative operation of said first and second rotary motors and said linear motor.

9. The method of claim 8, further comprising the steps of:
positioning said tip of said probe so that it forms a plurality of hemispherical paths of travel relative to said virtual point, in addition to said at least a first hemispherical path of travel by elevating said tip of said probe relative to said virtual point and by cooperative operation of said first and second rotary motors and said linear motor.

10. The method of claim 7, further comprising the steps of:
providing each of said motors in the form of a piezoelectric motor, each of which is provided with a piezo element; and
supplying resonant frequency excitation pulses of controlled duration to the respective piezo element of each of said motors.

11. The method of claim 10, further comprising the steps of:
electrically coupling a joystick to said control unit to enable manual control of said first, second, and third motors.

12. The method of claim 10, further comprising the steps of:
controlling the apparatus with a programmed computer.

13. The method of claim 12, further comprising the steps of:
mounting an optical encoder on each of said motors;
providing a digital signal processing controller;
controlling absolute rotational or linear coordinates of the motors by connecting said optical encoders and digital signal processing controller to said programmed computer so that said programmed computer controls the instantaneous rotational positions of the respective output shafts of first and second rotary motors as well as the instantaneous linear position of said probe;
whereby motion of the output shafts of the rotary and linear motors at specific angles and linear positions, respectively, is reproducible and within the accuracy of the respective motors.

14. The method of claim 7, further comprising the steps of:
providing an XYZ positioning device to enable a virtual point of said probe to be positioned at the point of application in three dimensional (3-D) space, as determined by the specifications of the XYZ positioning device so that when the point of application is reached, the angle of approach of said probe can be changed by rotational operation of either rotary motor while maintaining the position of said tip continuously at the point of application.

15. The method of claim 7, further comprising the step of:
providing a first motor for controlling an x-axis position of said platform;
providing a second motor for controlling a y-axis position of said platform; and
providing a third motor for controlling a z-axis position of said platform.

16. A rotational and translational micropositioning apparatus, comprising:
an output shaft of a first rotary motor and an output shaft of a second rotary motor being disposed in a horizontal plane in orthogonal relation to one another and being connected to one another by a right-angled bracket when said apparatus is in a position of repose;
an output shaft of a linear motor being disposed in a vertical plane in orthogonal relation to the respective output shafts of said first and second rotary motors when said apparatus is in said position of repose and being connected to the output shaft of said second rotary motor;
a probe of linear configuration being secured to said linear motor in parallel relation thereto and said probe having a tip;
a virtual point defined by intersection of respective longitudinal axes of symmetry of said output shafts of said first and second rotary motors and said linear motor;
whereby simultaneous rotation of said output shaft of said first rotary motor, said output shaft of said second rotary motor, and simultaneous displacement of said output shaft of said linear motor enable said probe to be positioned in an infinite plurality of positions of adjustment where said tip of said probe remains in juxtaposition with said virtual point;
and whereby said infinite plurality of positions of adjustment collectively define a cone where said tip of said probe defines the vertex of said cone.

* * * * *